United States Patent [19]

Mischenko et al.

[11] 4,179,470

[45] Dec. 18, 1979

[54] PROCESS FOR PRODUCING ANILINE WITH A PERMSELECTIVE PALLADIUM AND RUTHENIUM CATALYST

[76] Inventors: Alexandr P. Mischenko, Teply Stan, 2 mikroraion, korpus 24, kv. 426; Vladimir M. Gryaznov, Lomonosovsky prospekt, 14, kv. 504; Viktor S. Smirnov, Kutuzovsky prospekt, 26, kv. 555; Elena D. Senina, Sevastopolsky prospekt, 75, korpus 1, kv. 13; Iraida L. Parbuzina, Metrostroevskaya ulitsa, 3/14, kv. 44; Natalia R. Roshan, Yaroslavskoe shosse, 57, kv. 36; Viktoria P. Polyakova, ulitsa Trofimova, 15, kv. 201; Evgeny M. Savitsky, ulitsa Dmitria Ulyanova, DNR-3, kv. 13, all of Moscow, U.S.S.R.

[21] Appl. No.: 899,418

[22] Filed: Apr. 24, 1978

[30] Foreign Application Priority Data

Aug. 12, 1977 [SU] U.S.S.R. .......................... 2521297[I]

[51] Int. Cl.$^2$ ............................................. C07C 85/11
[52] U.S. Cl. ..................................... 260/580; 252/472
[58] Field of Search ......................... 260/580; 252/472

[56] References Cited

U.S. PATENT DOCUMENTS

| | | | |
|---|---|---|---|
| 3,177,258 | 4/1965 | Rylander et al. | 260/580 X |
| 3,455,845 | 7/1969 | Wicke et al. | 252/472 X |
| 3,962,337 | 6/1976 | Drake | 252/472 X |
| 4,005,143 | 1/1977 | Bohm et al. | 260/580 X |
| 4,026,944 | 5/1977 | Bohm et al. | 260/580 |

*Primary Examiner*—Winston A. Douglas
*Assistant Examiner*—John Doll
*Attorney, Agent, or Firm*—Haseltine, Lake & Waters

[57] ABSTRACT

A process for producing aniline, residing in a catalytic hydrogenation of nitrobenzene by using hydrogen in a gaseous phase at a temperature of from 20° to 260° C. and under atmospheric pressure, using a membrane catalyst which is essentially an alloy of palladium and ruthenium taken in a mass percent ratio of 88–98:12–2, respectively, permselective to hydrogen; hydrogenation being carried out by feeding nitrobenzene on the one side of the membrane catalyst and hydrogen, on the other side thereof. The process enables one to obviate purification of the end product from the residual catalyst and thereby to avoid losses of metals of the platinum group, as well as to effect hydrogenation under milder conditions without the formation of any by-products.

3 Claims, No Drawings

PROCESS FOR PRODUCING ANILINE WITH A PERMSELECTIVE PALLADIUM AND RUTHENIUM CATALYST

FIELD OF THE INVENTION

The present invention relates to processes for producing aromatic amino compounds, viz., aniline, by catalytic hydrogenation of aromatic nitro compounds, such as nitrobenzene. Aniline is used in making a variety of organic substances, aniline dyes, diverse azo dyes, for the synthesis of drugs, etc.

BACKGROUND OF THE INVENTION

Known in the art are some processes for producing aromatic aminocompounds, such as aniline by the hydrogenation of aromatic nitro compounds, e.g., nitrobenzene in a liquid phase by using hydrogen, with the use of a dispersed catalyst which is a metal of the platinum group, e.g., palladium, or said metal on a support, the hydrogenation process occurring at a temperature of from 20° to 100° C. and a pressure from 10 to 40 atm.

Said known processes, however, suffer from a number of substantial disadvantages, such as:
(1) The end product needs purification from the catalyst particles, which involves heavy losses of precious metals (viz., metals of the platinum group);
(2) The hydrogenation process is carried out at high pressure;
(3) The process is accompanied by the formation of a great deal of by-products, amounting to 10 percent.

OBJECT AND SUMMARY OF THE INVENTION

It is an object of the present invention to provide a process for producing aniline which would make it possible to dispense with purification of the end product from the catalyst and, thereby, to rule out any losses of metals of the platinum group.

It is another object of the present invention to provide such a process of the character set forth hereinabove that would enable hydrogenating nitrobenzene into aniline under milder conditions.

It is still another object of the present invention to provide such a process for the hydrogenation of nitrobenzene into aniline that would be free from any by-products.

In keeping with said and other objects the invention resides in a process for producing aniline by catalytic hydrogenation of nitrobenzene by means of hydrogen, wherein, according to the invention nitrobenzene is subjected to hydrogenation in a gaseous phase at a temperature of from 20° to 260° C., preferably at 120° to 200° C., and under atmospheric pressure, making use of a membrane catalyst which is essentially a Pd-Ru alloy, the components being taken in a mass percent ratio of 88–98:12–2, respectively, preferably 92–97:8–3, said catalyst being permselective to hydrogen, the hydrogenation process being carried out by feeding nitrobenzene vapors on the one side of the membrane catalyst, and hydrogen, on the other side there of.

The process of the invention features the following advantages:
(1) The process makes it possible to obviate purification of the end product from the residual catalyst and, thereby to rule out losses of precious metals (viz., metals of the platinum group), by using a membrane catalyst;
(2) The process of nitrobenzene hydrogenation into aniline is carried out under atmospheric pressure, which is attained by the use of a membrane catalyst permselective to hydrogen; the latter is fed to the reaction zone in a highly active atomic state;
(3) The hydrogenation process runs without the formation of any by-products inasmuch as application of the membrane catalyst enables one to maintain the hydrogen concentration on the surface of said catalyst within the limits required for the selective hydrogenation;
(4) The catalyst is resistant to the effect of hydrogen and nitrogen-containing compounds (viz., nitrobenzene and aniline), which is accounted for by the provision of ruthenium as the catalyst constituent.

DETAILED DESCRIPTION OF THE INVENTION

The process is carried into effect in a reaction vessel consisting of two chambers sealingly isolated from each other by a membrane catalyst which is in fact an alloy of palladium (88 to 98 mass percent) with ruthenium (2 to 12 mass percent), permselective to hydrogen. A temperature of from 20° to 260° C. is maintained inside said reaction vessel. Nitrobenzene vapors carried by the stream of an inert gas are fed from bubblers to one of the chambers of the reaction vessel, viz., the hydrogenation chamber, while hydrogen is fed to the other chamber of the vessel. The pressure in the hydrogenation chamber equals atmospheric pressure. It is in the hydrogenation chamber that the nitrobenzene vapors are free to react on the surface of the membrane catalyst with hydrogen diffusing through the membrane catalyst from the other chamber of the reaction vessel, to form ailine. The membrane catalyst can be provided as a foil 10 to 200$\mu$ thick, a film 0.1 to 10$\mu$ thick, or a thin-walled tube having a wall thickness from 10 to 200$\mu$. In the latter case one of the chambers (I) is established by the bore of the tube, while the other chamber (II) is established by the inner walls of the hydrogenation reactor and the other walls of the tube. Nitrobenzene vapors and hydrogen can be fed to either of the chambers, i.e. when nitrobenzene vapors are fed to chamber (I) hydrogen is fed to chamber (II), and vice versa.

The amount of hydrogen diffusing through the membrane catalyst should be 1.5 to 2 times the stoichiometric quantity, and is controlled by the temperature in the reaction vessel, the pressure of hydrogen and the rate of hydrogen flow to the chamber. The amount of nitrobenzene fed to the hydrogenation chamber of the reaction vessel is regulated by the rate of nitrobenzene flow and the temperature in the bubblers.

To promote understanding of the present invention the following examples illustrate its practical embodiment. In examples not specifying hydrogen pressure, atmospheric pressure is implied.

EXAMPLE 1

Nitrobenzene is hydrogenated in a reaction vessel shaped as a metal shell subdivided into two halves (chambers) sealingly isolated from each other by the membrane catalyst permselective to hydrogen and made as an alloy of palladium (90 mass percent) and ruthenium (10 mass percent). The membrane catalyst is shaped as a foil 100$\mu$ thick and 18 cm$^2$ in area. Each of the chambers has sleeves for the parent reagents to feed in and to let out the reaction products. Once the temperature in the reaction vessel has been raised to 170° C., hydrogen (at a flow rate of 0.5 ml/s) is fed to one of the chambers, while nitrobenzene vapors taken from bubblers at a temperature of 50° C., are fed to the other (hydrogenation) chamber in a stream of argon at a flow rate of 0.47 ml/s. The pressure in the hydrogenation chamber equals atmospheric pressure. The space rate of feed of nitrobenzene per unit area of the catalyst is 39 ml/min·m$^2$. The duration of the hydrogenation process is 3 hours. Hydrogen is made to diffuse in an atomic state through the membrane catalyst into the hydrogenation chamber to which nitrobenzene vapors are fed, whereupon hydrogen enters the reaction with nitrobenzene on the catalyst surface to give aniline.

The reaction products leaving the reactor, are subjected to analysis on a chromatograph having a 1.5-m column filled with diatomite impregnated with polymethylsiloxane (12 mass percent). According to chromatographic analysis a complete conversion of nitrobenzene to aniline and water is achieved. Within a three-hour period the catalyst activity remains constant.

EXAMPLE 2

Nitrobenzene is subjected to hydrogenation as described in Example 1 for 1 hour at a temperature of 30° C., with a space rate of feed of nitrobenzene vapors and hydrogen equal to 0.99 ml/s and 0.5 ml/s, respectively. The temperature in the bubblers is 90° C. According to the data of chromatography, the liquid catalysate is found to contain aniline and nitrobenzene in a molar ratio of 10:90, respectively. No by-products are present. The catalyst activity is found to remain constant throughout the hydrogenation process.

EXAMPLE 3

Nitrobenzene is subjected to hydrogenation as described in Example 1 at a temperature of 70° C. and a space rate of feed of nitrobenzene vapors and hydrogen equal to 1.09 m/s and 0.5 ml/s, respectively. The temperature in the bubblers is 70° C. According to the data of chromatography, the liquid catalysate is found to contain aniline and nitrobenzene in a molar ratio of 36:64, respectively. No by-products are present. Within a three-hour period the catalyst activity remains constant.

EXAMPLE 4

Nitrobenzene is subjected to hydrogenation as described in Example 1 for 4 hours at a temperature of 120° C. and a space rate of feed of nitrobenzene vapors and hydrogen equal to 0.48 ml/s and 0.5 ml/s, respectively. The temperature in the bubblers is 50° C. According to the data of chromatography, the liquid catalysate is found to contain aniline and nitrobenzene in a molar ratio of 68:32, respectively. No reaction by-products are present. The catalyst activity remains constant throughout the hydrogenation process.

EXAMPLE 5

Nitrobenzene is subjected to hydrogenation as described in Example 1 for 8 hours at a temperature of 260° C., and a space rate of feed of nitrobenzene vapors and hydrogen equalling 1 ml/s and 0.5 ml/s, respectively. The nitrobenzene vapors are fed from bubblers heated to 100° C. The resulting catalysate is found to consist of only aniline and water when subjected to chromatographic analysis. The catalyst activity remains constant within 8 hours.

EXAMPLE 6

Nitrobenzene is subjected to hydrogenation as described in Example 1 using the membrane catalyst which is an alloy of 94 mass percent Pd and 6 mass percent Ru. The thickness of the membrane catalyst (foil) is 90$\mu$, the area, 18 cm$^2$. The temperature in the hydrogenation reactor is 200° C., the duration of the process, 1.5 hours. The space rate of feed of nitrobenzene vapors from bubblers heated to 122° C. to the reactor hydrogenation chamber is 0.85 ml/s, the space rate of hydrogen feed to the other reactor chamber, 0.5 ml/s. For the initial 0.5 hour the catalysate is found to contain aniline and nitrobenzene in a molar ratio of 99.3:0.7, respectively; within the following hour the molar ratio of the aniline and nitrobenzene in the catalysate equals 99.1:0.9, respectively. No reaction by-products are present.

EXAMPLE 7

Nitrobenzene is subjected to hydrogenation as described in Example 1 using the membrane catalyst which is an alloy of Pd (98 mass percent) and Ru (2 mass percent), the thickness of the membrane catalyst (foil) being 100$\mu$ and the area, 1.2 cm$^2$. The temperature in the hydrogenation reactor is maintained at 100° C. The duration of the process is 3 hours. The space rate of feed of nitrobenzene vapors from bubblers heated to 70° C. to the reactor hydrogenation chamber is 0.1 ml/s, the pressure in said chamber being equal to atmospheric pressure; the space rate of feed of hydrogen to the other chamber of the reactor is 0.5 ml/s, the hydrogen pressure in said chamber being 2 atm. Analysis of the catalysate resulting from the hydrogenation process has demonstrated the molar ratio of the resultant aniline and the nonconverted nitrobenzene to be 71.4:28.6, respectively. No reaction by-products are present.

EXAMPLE 8

Nitrobenzene is subjected to hydrogenation in a reaction vessel using the membrane catalyst shaped as a 2.5 m long, 1 mm dia. tube, featuring a wall thickness of 100$\mu$. The material of the membrane catalyst is an alloy incorporating 94 mass percent Pd and 6 mass percent Ru. The hydrogenation process runs at a temperature in the reactor equal to 20° C. for a period of 4 hours. Nitrobenzene vapors are fed from bubblers having the same temperature as the reactor vessel, to the hydrogenation chamber defined by the inner reactor walls and the outer walls of the tube (i.e., the membrane catalyst) at a space rate of flow equal to 0.3 ml/s, the pressure in the hydrogenation chamber being equal to atmospheric pressure. The space rate of hydrogen feed to the other chamber of the reactor (i.e., the tube) equals 0.5 ml/s, the hydrogen pressure in said chamber being 12 atm. The resultant catalysate exhibits the molar ratio of aniline and nitrobenzene to be 48:52, respectively. No reaction by-products are present.

Pd-Ru alloys containing up to 12 mass percent Ru, are known to constitute a number of solid solutions; that is why the properties of said alloys will change, as a rule, monotonically The catalytic properties of a Pd-based alloy containing 12 mass percent Ru differ but slightly from those of a palladium-ruthenium alloy featuring a 10 mass percent content of the latter. Inasmuch as a substantial feature for carrying out the herein proposed process for aniline production is the permeability of the membrane catalyst to hydrogen, it should be noted that, as the percentage of ruthenium in Pd-Ru alloys increases, permeability of the catalyst to hydrogen reaches a maximum, characteristic of alloys containing 3 to 8 mass percent Ru, whereas permeability of an alloy having 12 mass percent Ru is still high enough to realize the process for aniline production.

What is claimed is:

1. A process for producing aniline, comprising subjecting nitrobenzene to catalytic hydrogenation using gaseous hydrogen at a temperature of from 20° to 260° C. and under atmospheric pressure, using a membrane catalyst which is essentially an alloy containing palladium and ruthenium, taken in a mass percent ratio of 88–98:12–2, respectively, said catalyst being permselective to hydrogen; the hydrogenation process being carried out by feeding nitrobenzene vapors on one side of the membrane catalyst and hydrogen, on the other side thereof.

2. The process as claimed in claim 1, wherein the hydrogenation is carried out at 120° to 200° C.

3. The process as claimed in claim 1, wherein the membrane catalyst is an alloy of palladium and ruthenium taken in a mass percent ratio of 92–97:8–3, respectively.

* * * * *